(12) United States Patent
Wotherspoon et al.

(10) Patent No.: US 10,314,678 B2
(45) Date of Patent: Jun. 11, 2019

(54) CLEANING DEVICE FOR REMOVABLE DENTAL APPLIANCES

(71) Applicant: Dr Mark's Hygenie Pty Ltd, Wagga Wagga, New South Wales (AU)

(72) Inventors: Mark Wotherspoon, Wagga Wagga (AU); Stephen Plakotaris, Leichhardt (AU)

(73) Assignee: Dr Mark's HyGenie Pty Ltd, Wagga Wagga, New South Wales (AU)

( * ) Notice: Subject to any disclaimer, the term of this patent is extended or adjusted under 35 U.S.C. 154(b) by 0 days.

(21) Appl. No.: 15/552,731

(22) PCT Filed: Jan. 23, 2017

(86) PCT No.: PCT/AU2017/050052
§ 371 (c)(1),
(2) Date: Aug. 22, 2017

(87) PCT Pub. No.: WO2017/173479
PCT Pub. Date: Oct. 12, 2017

(65) Prior Publication Data
US 2018/0110600 A1    Apr. 26, 2018

(30) Foreign Application Priority Data

Apr. 5, 2016 (AU) ................................ 2016901263

(51) Int. Cl.
*A46B 7/08* (2006.01)
*A45D 44/20* (2006.01)
(Continued)

(52) U.S. Cl.
CPC .......... *A61C 17/036* (2013.01); *A46B 5/0004* (2013.01); *A46B 5/026* (2013.01);
(Continued)

(58) Field of Classification Search
CPC ...... A61C 17/036; A63B 47/04; A45D 44/20; A46B 13/00; A46B 13/08; A46B 13/008;
(Continued)

(56) References Cited

U.S. PATENT DOCUMENTS

| 1,845,315 A | 2/1932 | Meikle |
|---|---|---|
| 3,564,636 A | 2/1971 | Tomer |

(Continued)

FOREIGN PATENT DOCUMENTS

DE          203 18 762          6/2004

*Primary Examiner* — Mark Spisich
(74) *Attorney, Agent, or Firm* — Hamre, Schumann, Mueller & Larson, P.C.

(57) ABSTRACT

A cleaning device for cleaning a removable dental appliance is described. The device includes a rotatable upper cleaning brush having a plurality of downwardly protruding bristles for cleaning an upper surface of a removable dental appliance. The device also includes a lower dental appliance holder for holding the dental appliance and which is used in connection with the rotatable upper cleaning brush to limit movement of the dental appliance relative to the rotatable upper cleaning brush wherein, in use, a cleaning action can be applied to the dental appliance by rotating the rotatable upper cleaning brush relative to the dental appliance. The cleaning device further includes a casing connector for temporarily rotatably interconnecting the rotatable upper cleaning brush and the lower dental appliance holder so as to form a single integrated unit when assembled.

20 Claims, 7 Drawing Sheets

(51) Int. Cl.
*A46B 13/08* (2006.01)
*A61C 17/00* (2006.01)
*A46B 5/00* (2006.01)
*A46B 5/02* (2006.01)

(52) U.S. Cl.
CPC ............... *A46B 7/08* (2013.01); *A46B 13/08* (2013.01); *A45D 44/20* (2013.01); *A46B 2200/1073* (2013.01)

(58) Field of Classification Search
CPC .... A46B 7/00; A46B 7/06; A46B 7/08; A46B 9/00; A46B 9/02; A46B 9/028; A46B 9/04; A46B 9/045; A46B 15/00; A46B 2200/1073
USPC ....... 15/21.1, 21.2, 160, 167.1, 167.2, 205.2
See application file for complete search history.

(56) References Cited

U.S. PATENT DOCUMENTS

| | | |
|---|---|---|
| 4,984,323 A | 1/1991 | Digby |
| 5,298,077 A | 3/1994 | Saarela et al. |
| 9,198,745 B1 | 12/2015 | Trahan |

CLEANING DEVICE FOR REMOVABLE DENTAL APPLIANCES

FIELD OF THE INVENTION

The present invention relates to a cleaning device for removable dental appliances and relates particularly, though not exclusively, to a cleaning device for cleaning, storing and protecting removable dental appliances.

BACKGROUND TO THE INVENTION

The present invention was initially developed to overcome the problems faced by all denture wearers, particularly elderly people and aged care facilities, with respect to the cleaning of dentures. Typically elderly people and/or their carers clean dentures in hand with a brush, often using an incorrect cleaning solution (e.g. toothpaste).

The conventional 'brushing' method, which is considered the gold standard, is not simple, straightforward, or safe, nor does it provide a consistently hygienic outcome. This method uses a brush that is similar in design to a conventional tooth brush, and requires the dentures be hand-held, brushed and rinsed clean by either (a) a somewhat less dextrous, often elderly, person, or (b) a busy carer. Dentures are very expensive to replace or repair and can easily be damaged when dropped. Replacement or even the simplest repair of broken dentures can offer significant clinical challenges for patients who display varying degrees of muscle dysfunction [e.g. dysphagia] or varying levels of cognitive impairment [e.g. dementia].

Inadequate cleaning of oral appliances equates to poor oral hygiene. The detrimental effects of poor oral hygiene on general health and its contribution to numerous diseases of the mouth are well documented in the scientific literature and are universally accepted.

Prior art cleaning devices for dentures include various kinds of brushes, holders, containers, cleaning solutions, sanitising solutions, soaking baths, ultra-sonic and ultra-violet baths. However each of these known products currently available does only one thing: it either 'cleans,' 'stores,' or 'protects' the dentures. Nothing currently available is able to effectively combine the functions of 'cleaning, storing and protecting'.

U.S. Pat. No. 3,564,636 (Tomer) issued in 1971 is for a brushing device for dentures that comprises first and second discs with brush bristles secured thereto, the discs being non-rotatably received in respective first and second cup-shaped containers. The open mouth of each of the cup-shaped containers is designed to be received in "interfitting relationship" with the other so as to permit "relative rotation with respect to the other." A denture is placed between the brushes and a cleaning action is performed by relatively rotating the cup-shaped containers with the fingers of both hands in contact therewith. There are no perforations in the cup-shaped containers to permit fluid flow into the region between the brushes. The device of Tomer is designed simply as a cleaning device.

U.S. Pat. No. 5,298,077 (Saarela) issued in 1994 is for a cleaning device for dental appliances and for a method. The device of Saarela is a hollow circular case formed from two coacting elements, a top half and a bottom half, which engage with one another to form a sealed case. Openings are provided in a peripheral wall of each half, and bristle tufts are seated between the openings and from substantially the whole interior surface of the case. As shown in FIG. 5, the two halves of the case of Saarela can be twisted, while holding it under running water, to effect a cleaning action of a dental appliance held within the case. The case can also be used for storing the dental appliance after cleaning (see column 3, line 33).

One of the problems with these prior art cleaning devices is that there is no facility for accommodating different sized dental appliances within the device.

The present invention was developed with a view to providing a more efficient denture cleaning device that can be easily used by an elderly person or a busy carer. The device may also provide a purpose-built system for properly cleaning, storing and protecting dentures. However during the initial development phases applications for all other types of removable dental appliances were also developed, using the same basic device design and 'technology'. At this stage, it is anticipated that various embodiments of the invention may be used for cleaning all types of removable dental appliances.

The term 'removable dental appliance' is not limited to, but includes the following types of intra-oral appliances:
    Sports and protective mouth guards (boil and bite or professionally customised).
    Occlusal Splints
    Mandibular Advancement Devices
    Sleep Apnoea and Anti Snoring Devices
    Full and Partial Dentures
    Orthodontic Retainers
    Removable orthodontic alignment devices
    Tooth whitening stents References to prior art in this specification are provided for illustrative purposes only and are not to be taken as an admission that such prior art is part of the common general knowledge in Australia or elsewhere.

SUMMARY OF THE INVENTION

According to one aspect of the present invention there is provided a cleaning device for cleaning a removable dental appliance, the device comprising:
    a rotatable upper cleaning brush comprising a plurality of downwardly protruding bristles for cleaning an upper surface of a removable dental appliance;
    a lower dental appliance holder for holding the dental appliance and which is used in connection with the rotatable upper cleaning brush to limit movement of the dental appliance relative to the rotatable upper cleaning brush;
    a casing connector for temporarily rotatably interconnecting the rotatable upper cleaning brush and the lower dental appliance holder so as to form a single integrated unit wherein, in use, a cleaning action can be applied to the dental appliance by rotating the rotatable upper cleaning brush and/or the lower dental appliance holder relative to the dental appliance; and
    wherein the casing connector comprises a generally cylindrical housing for enclosing a cleaning region between the rotatable upper cleaning brush and the lower dental appliance holder.

Preferably the cylindrical housing is manufactured of a substantially transparent material wherein, in use, the cleaning region between the rotatable upper cleaning brush and the lower dental appliance holder is generally visible to the user during use. Preferably the cylindrical housing comprises a plurality of perforations so as to permit fluid to flow through the casing connector to the dental appliance held in the cleaning region between the rotatable upper cleaning brush and the lower dental appliance holder.

Preferably the rotatable interconnection is facilitated by a raised guide rail on the upper cleaning brush and first and second internal grooves in the casing connector. Advantageously the cleaning device further comprises a locking mechanism for locking the casing connector to the rotatable upper cleaning brush to permit rotation of the upper cleaning brush relative to the casing connector without the device coming apart. Typically the locking mechanism comprises a 'push, turn and click' locking mechanism provided adjacent to the raised guide rail on the rotatable upper cleaning brush. Preferably the 'push, turn and click' locking mechanism comprises a plurality of lock protrusions provided on the upper cleaning brush, and a matching plurality of interlocking recesses provided in at least one of the first and second internal grooves of the casing connector.

Preferably both the rotatable upper cleaning brush and the lower dental appliance holder can be handheld, and the relative rotation of the rotatable upper cleaning brush and/or the lower dental appliance holder can be effected by a simple back and forth twisting action of the hands.

Preferably the lower dental appliance holder comprises a lower cleaning brush having a plurality of upwardly protruding bristles for cleaning a lower surface of the dental appliance whereby, in use, rotation of the rotatable upper cleaning brush and of the lower cleaning brush relative to the dental appliance ensures that a simultaneous cleaning action is applied to both the upper and the lower surfaces of the dental appliance. Preferably both the rotatable upper cleaning brush and the lower dental appliance holder are of substantially circular configuration.

In one embodiment an annular lip is provided on the lower dental appliance holder, the annular lip being received in one of the first and second internal grooves of the casing connector by a simple friction fit since the lower dental appliance holder is not required to rotate relative to the casing connector.

In a more preferred embodiment the rotatable interconnection is also facilitated by a raised guide rail on the lower cleaning brush and a locking mechanism for locking the casing connector to the lower cleaning brush to permit rotation of the lower cleaning brush relative to the casing connector without the device coming apart.

Preferably the rotatable upper cleaning brush further comprises an upper base component having the downwardly protruding bristles provided in connection with a lower side of the base component, and a handle provided in connection with an upper side of the base component. Preferably the handle is ergonomically designed for a left-handed or right-handed user as required. Advantageously the handle is manufactured from a suitable soft, non-slip material to provide a comfortable and secure grip in use when either wet or dry.

Preferably the lower cleaning brush further comprises a lower base component having the upwardly protruding bristles provided in connection with an upper side of the base component, and a handle provided in connection with a lower side of the base component.

Advantageously both the rotatable upper cleaning brush and the rotatable lower cleaning brush are of substantially identical design and construction.

Advantageously the downwardly and upwardly protruding bristles provided on the upper and lower cleaning brushes respectively are adapted to interleave as the upper and lower cleaning brushes are rotated relative to each other to ensure that deep, harder-to-reach areas of the dental appliance are reached and thoroughly cleaned. Optionally the bristles on either one or both of the upper and lower cleaning brushes are tapered so that during relative rotation they intermittently interleave.

Preferably the bristles on either one or both of the upper and lower cleaning brushes are arranged in clusters, including a plurality of peripheral clusters, and a single central cluster of bristles of relatively increased height surrounded by troughs formed by bristles of relatively reduced height in between so as to form one or more recesses within which the removable dental appliance can be more readily accommodated.

Throughout the specification, unless the context requires otherwise, the word "comprise" or variations such as "comprises" or "comprising", will be understood to imply the inclusion of a stated integer or group of integers but not the exclusion of any other integer or group of integers. Likewise the word "preferably" or variations such as "preferred", will be understood to imply that a stated integer or group of integers is desirable but not essential to the working of the invention.

BRIEF DESCRIPTION OF THE DRAWINGS

The nature of the invention will be better understood from the following detailed description of several specific embodiments of a dental cleaning device, given by way of example only, with reference to the accompanying drawings, in which.

DETAILED DESCRIPTION OF PREFERRED EMBODIMENTS

Figure 1:
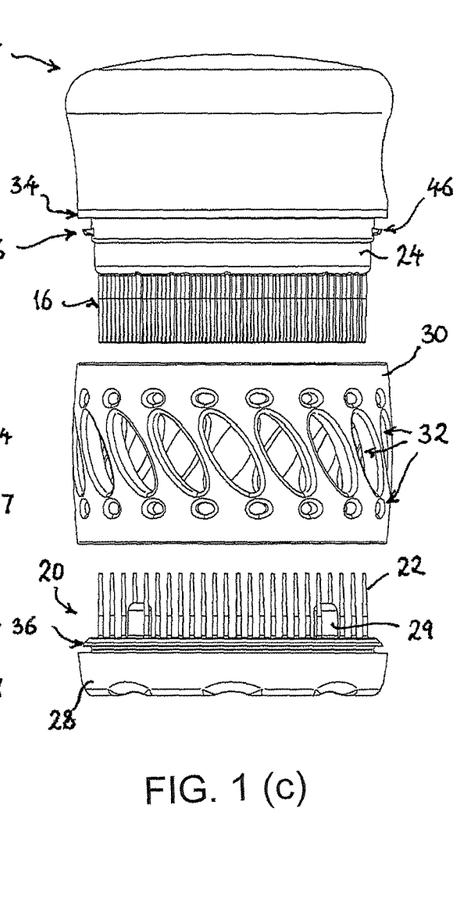
FIG. 1(a) is a side elevation view of a first embodiment of a dental cleaning device in accordance with the present invention.
FIG. 1(b) is a section view of the cleaning device of FIG. 1 through the line E-E in FIG. 1(a)
FIG. 1(c) is an exploded view of the cleaning device of FIG. 1.

A first embodiment of a cleaning device 10, for cleaning a removable dental appliance (not shown), in accordance with the invention, as illustrated in FIGS. 1(a) to 1(c), comprises a rotatable upper cleaning brush 14 comprising a plurality of downwardly protruding bristles 16 for cleaning an upper surface of the removable dental appliance. This embodiment is designed particularly for larger dental appliances, such as full and partial dentures, etc. The rotatable upper cleaning brush 14 is preferably of substantially circular configuration. Preferably the rotatable upper cleaning brush 14 further comprises an upper base component 24 having the downwardly protruding bristles 16 provided in connection with a lower side of the base component 24, as can be seen most clearly in FIGS. 1(b) and 1(c). The base component 24 is preferably manufactured as a separate component from a hard plastics material. In this embodiment the downwardly protruding bristles 16 are moulded separately, from a suitably resilient rubber, silicon or plastics material with the required stiffness to effect the cleaning action. The bristles 16 protrude from a web 17 of the same material, which clips onto the lower side of the base component 24, as can be seen most clearly in FIG. 1(b).

An upper handle 26 is provided in connection with an upper side of the base component 24. Preferably the upper handle 26 is ergonomically designed for a left-handed or right-handed user as required. In this embodiment the handle 26 is manufactured as a separate component from a soft, non-slip silicon material to provide a comfortable and secure grip in use when either wet or dry. The handle 26 clips onto the upper side of the base component 24, as can be seen most clearly in FIG. 1(b).

The cleaning device 10 further comprises a lower dental appliance holder 18 for holding the dental appliance and which is used in connection with the rotatable upper cleaning brush to limit movement of the dental appliance relative to the rotatable upper cleaning brush 14 wherein, in use, a cleaning action can be applied to the dental appliance by rotating the rotatable upper cleaning brush 14 and/or the lower dental appliance holder 18 relative to the dental appliance. Preferably both the rotatable upper cleaning brush 14 and the lower dental appliance holder 18 are dimensioned so to be capable of being handheld, and the relative rotation of the rotatable upper cleaning brush 14 and/or the lower dental appliance holder 18 can be effected by a simple back and forth twisting action of the hands.

In this embodiment the lower dental appliance holder 18 is also of substantially circular configuration, and comprises a lower cleaning brush 20 comprising a plurality of upwardly protruding bristles 22 for cleaning a lower surface of the dental appliance. In use, rotation of the rotatable upper cleaning brush 14 and the lower cleaning brush 20 relative to the dental appliance ensures that a simultaneous cleaning action is applied to both the upper and the lower surfaces of the dental appliance.

Preferably the lower cleaning brush 20 further comprises a lower base component 21 having the upwardly protruding bristles 22 provided in connection with an upper side of the base component, and a lower handle 28 provided in connection with a lower side of the base component 21. Preferably the lower cleaning brush 20 further comprises an annular lip 36 provided on the base component 21. Advantageously the annular lip 36 is tapered, as can be seen most clearly in FIGS. 1(b) and 1(c). Preferably in this embodiment the lower base component 21, upwardly protruding bristles 22 and lower handle 28 are all moulded of a suitably resilient plastics material as a single integrated component.

Preferably the upwardly protruding bristles 22 on the lower cleaning brush 20 include a plurality of anti-rotation pillars 29 of increased size, which are adapted to limit movement of the removable dental appliance during the cleaning action. Typically the anti-rotation pillars 29 are of increased height, diameter and stiffness relative to the upwardly protruding bristles 22, as can be clearly seen in FIG. 1(c). The anti-rotation pillars 29 provide a limit to the degree of rotation of the dental appliance that occurs when the rotatable upper cleaning brush 14 cleans the upper surface of the appliance. As the rotatable upper cleaning brush 14 is "worked" in a clockwise/anticlockwise manner, the appliance may move across the lower cleaning brush 20 until it engages with one of the anti-rotation pillars 29 and reaches a limit, and then it may move back again until it engages with another one of the anti-rotation pillars 29 and reaches a new limit. The appliance may thus move back and forth within limits during the cleaning action. This facilitates the simultaneous cleaning action on "all surfaces" of the dental appliance.

Typically the cleaning device 10 further comprises a casing connector 30 for temporarily rotatably interconnecting the rotatable upper cleaning brush 14 and the lower cleaning brush 20 so as to form a single integrated unit or "caddy" when assembled. Preferably the casing connector comprises a cylindrical housing 30 for enclosing the downwardly protruding bristles 16 and the upwardly protruding bristles 22 in a cleaning region between the rotatable upper cleaning brush 14 and the lower cleaning brush 20. The cylindrical housing 30 is preferably provided with a plurality of perforations 32 so as to permit fluid to flow through the casing connector into the cleaning region between the rotatable upper cleaning brush 14 and the lower cleaning brush 20.

Figure 5:
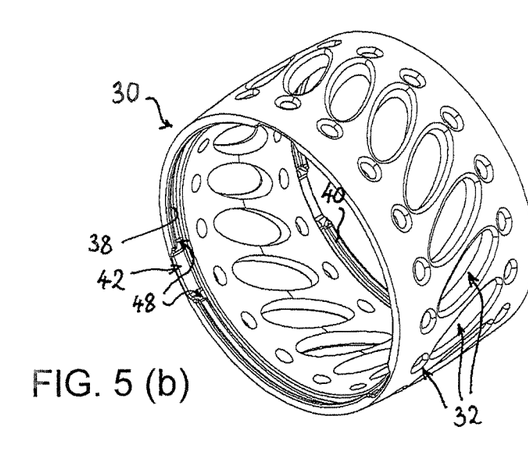
FIG. 5(a) is a horizontal side elevation of a casing connector for the cleaning device of FIG. 1 and the cleaning device of FIG. 2.
FIG. 5(b) is a side perspective view of the casing connector of FIG. 5(a)
FIG. 5(c) is a top plan view of the casing connector of FIG. 5(a)
FIG. 5(d) is a section view of the casing connector through the line E-E in FIG. 5(c)

Preferably the rotatable interconnection with the casing connector 30 is facilitated by a raised guide rail 34 provided on the base component 24 of the rotatable upper cleaning brush 14, as can be seen most clearly in FIG. 1(b). In its assembled position, an upper edge of the cylindrical housing 30 abuts against the raised guide rail 34, as shown in FIGS. 1(a) and 1(b). The cylindrical housing 30 is provided with first and second internal grooves 38, 40, as can be seen most clearly in FIGS. 5(b) and 5(d).

Typically the cleaning device 10 further comprises a locking mechanism 44 for locking the casing connector 30 to the rotatable upper cleaning brush 14 to permit rotation of the upper cleaning brush relative to the lower cleaning brush without the device coming apart. Typically the locking mechanism 44 comprises a 'push, turn and click' locking mechanism provided adjacent to the raised guide rail 34 on the rotatable upper cleaning brush. The 'push, turn and click' locking mechanism 44 comprises a plurality (in this embodiment three) lock protrusions 46 provided on the upper base component 24, and a matching plurality of interlocking recesses 42 provided in the internal grooves 38 and 40 of the casing connector 30. The lock protrusions 46 are provided adjacent to the raised guide rail 34 and are adapted to be slidably received in either one of the first and second internal grooves 38 and 40.

Advantageously the interlocking recesses 42 are provided in both the first and second internal grooves 38, 40, as the casing connector 30 is designed to be substantially symmetrical about a central horizontal plane, represented by the line A-A in FIG. 5(a). This enables the casing connector 30 to be connected to the upper and lower cleaning brushes 14 and 20 in either orientation in the assembled device 10. Within the grooves 38 and 40, on either side of the interlocking recesses 42, first and second stops 48 are provided, as shown in FIGS. 5(b) and 5(d). The stops 48 limit the extent of rotation of the rotatable upper cleaning brush 14 to about 120°.

In order to rotatably connect the rotatable upper cleaning brush 14 to the casing connector 30 the lock protrusions 46 are first aligned with the interlocking recesses 42. Then the cleaning brush 14 and casing connector 30 are pushed together and rotated relative to each other, so that the lock protrusions 46 ride over stops 48 provided at the sides of the interlocking recesses 42, and thereby the upper cleaning brush 14 and the casing connector 30 'lock' together. Once the lock protrusions 46 are received in the internal groove 38 or 40, they are free to slidably move in the grooves between the stops 48.

A straight rotation action of the upper cleaning brush 14 will not release from the guide rail 34. The rotation of the rotatable upper cleaning brush 14 reaches its limit when the lock protrusions 46 strike the stops 48. The rotatable upper cleaning brush 14 would then be rotated back the other way until the lock protrusions 46 again reach the stops 48. This back and forth rotation of the upper cleaning brush relative to the casing connector 30 is a preferred cleaning cycle.

To release the 'push, turn and click' locking mechanism 44, the upper base component 24 of the upper cleaning brush 14 must be slightly depressed (squeezed) so that the lock protrusions 46 "duck" under the stops 48 and can thus be realigned with the interlocking recesses 42 to release the upper cleaning brush 14 from the casing connector 30.

Assembly of the lower dental appliance holder 18 is somewhat different, as in this embodiment the lower cleaning brush 20 is not required to rotate relative to the casing connector 30. In this case, the annular lip 36, provided on the lower base component 21 of the lower cleaning brush 20, is received in the other one of the internal grooves 38, 40. The annular lip 36 is fitted to the casing connector 30 by a simple friction fit between the hard casing connector 30 and the resilient base component 21. The casing connector 30 is pushed down onto the base component 21 by hand pressure, so that the tapered annular lip 36 is squashed until it is received in the internal groove of the casing connector. This provides quite a firm fit, but the lower cleaning brush 20 and casing connector 30 can still be pulled apart as separate components if needs be.

Advantageously, in its assembled condition, the cleaning device 10 effectively 'locks' a dental appliance in place inside of the 'caddy-like' cylindrical housing 30, in the cleaning region between the rotatable upper cleaning brush 14 and the lower cleaning brush 20. The cylindrical housing 30 is of a diameter and size that it sits comfortably in a full-hand grip. It is ergonomically designed and protects the dental appliance from any damage that may otherwise occur from dropping or incorrectly holding the appliance while brushing.

The downwardly and upwardly protruding bristles 16, 22 provided on the upper and lower cleaning brushes 14, 20 respectively may be arranged edge to edge, so that the ends of the respective sets of bristles 16, 22 are just touching. However the downwardly and upwardly protruding bristles 16, 22 are preferably of a length so that the ends of the respective sets of bristles are adapted to interleave as the upper and lower cleaning brushes are rotated relative to each other, as shown in FIG. 1(b). This interleaving ensures that deep, harder-to-reach areas on the upper and lower surfaces of the dental appliance are reached and thoroughly cleaned. Optionally the lengths of the bristles on either one or both of the upper and lower cleaning brushes 14, 20 are tapered so that during relative rotation they intermittently interleave. Optional tapering of the bristles 16, 22 is evident in FIG. 1(c).

A second embodiment of a cleaning device 50, for cleaning a removable dental appliance (not shown), in accordance with the invention, is illustrated in FIGS. 2(a) to 7(d). The cleaning device 50 comprises a rotatable upper cleaning brush 14 having a plurality of downwardly protruding bristles 16 for cleaning an upper surface of the removable dental appliance. This embodiment is also designed for larger dental appliances, such as full or partial dentures, etc. The cleaning device 50 is similar to the first embodiment of the cleaning device 10, and therefore the like parts will be identified using the same reference numerals and will not necessarily be described again in detail. The rotatable upper cleaning brush 14 preferably further comprises an upper base component 24 having the downwardly protruding bristles 16 provided in connection with a lower side of the base component 24, as can be seen most clearly in FIGS. 2(d), 3 and 4.

Figure 6:
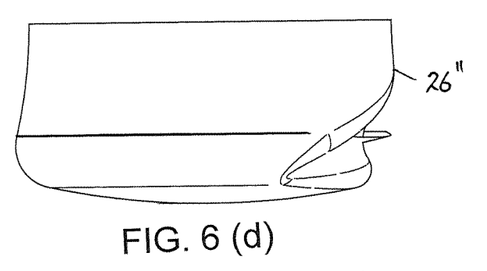
FIG. 6(a) is a top plan view of an alternative handle design for the cleaning device of FIG. 6.
FIG. 6(b) is a side elevation view of the handle shown in FIG. 6(a)
FIG. 6(c) is a perspective view of the handle shown in FIG. 6(a)
FIG. 6(d) is a side elevation of the handle shown in FIG. 6(a)

An upper handle 26' is provided in connection with an upper side of the base component 24. The handle 26' clips onto the upper side of the base component 24, as can be seen most clearly in FIGS. 2(d), 3 and 4. The handle 26' can be replaced with a different type of handle if required. FIG. 6 illustrates another type of handle 26" which provides a more ergonomically comfortable handgrip for the user. Preferably the handle 26" is ergonomically designed for a left-handed or right-handed user as required. In this embodiment the handle 26" is manufactured as a separate component from a soft, non-slip silicon material to provide a comfortable and secure grip in use when either wet or dry.

In this embodiment of the cleaning device 50 the lower dental appliance holder 18 is also of substantially circular configuration, and comprises a lower cleaning brush 20 having a plurality of upwardly protruding bristles 22 for cleaning a lower surface of the dental appliance. In use, during relative rotation of the rotatable upper cleaning brush 14, rotation of the lower cleaning brush 20 relative to the dental appliance ensures that a simultaneous cleaning action is applied to both the upper and the lower surfaces of the dental appliance.

Figure 2:
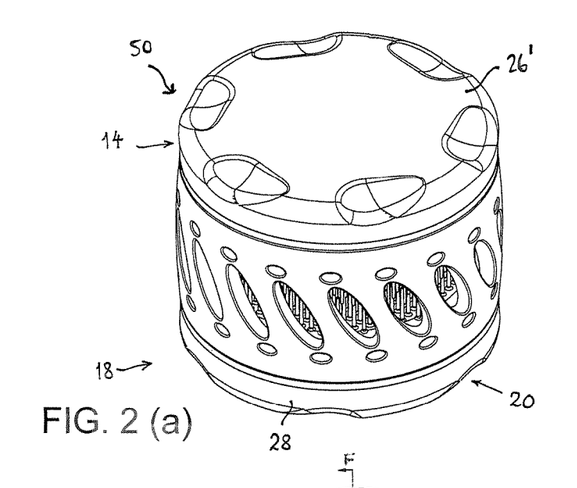
FIG. 2(a) is a top perspective view of a second embodiment of a dental cleaning device in accordance with the present invention.
FIG. 2(b) is a side elevation view of the cleaning device of FIG. 2(a)
FIG. 2(c) is a top plan view of the cleaning device of FIG. 2(a)
FIG. 2(d) is a section view of the cleaning device of FIG. 2(a) through the line F-F in FIG. 2(c)
Figures 3, 4:
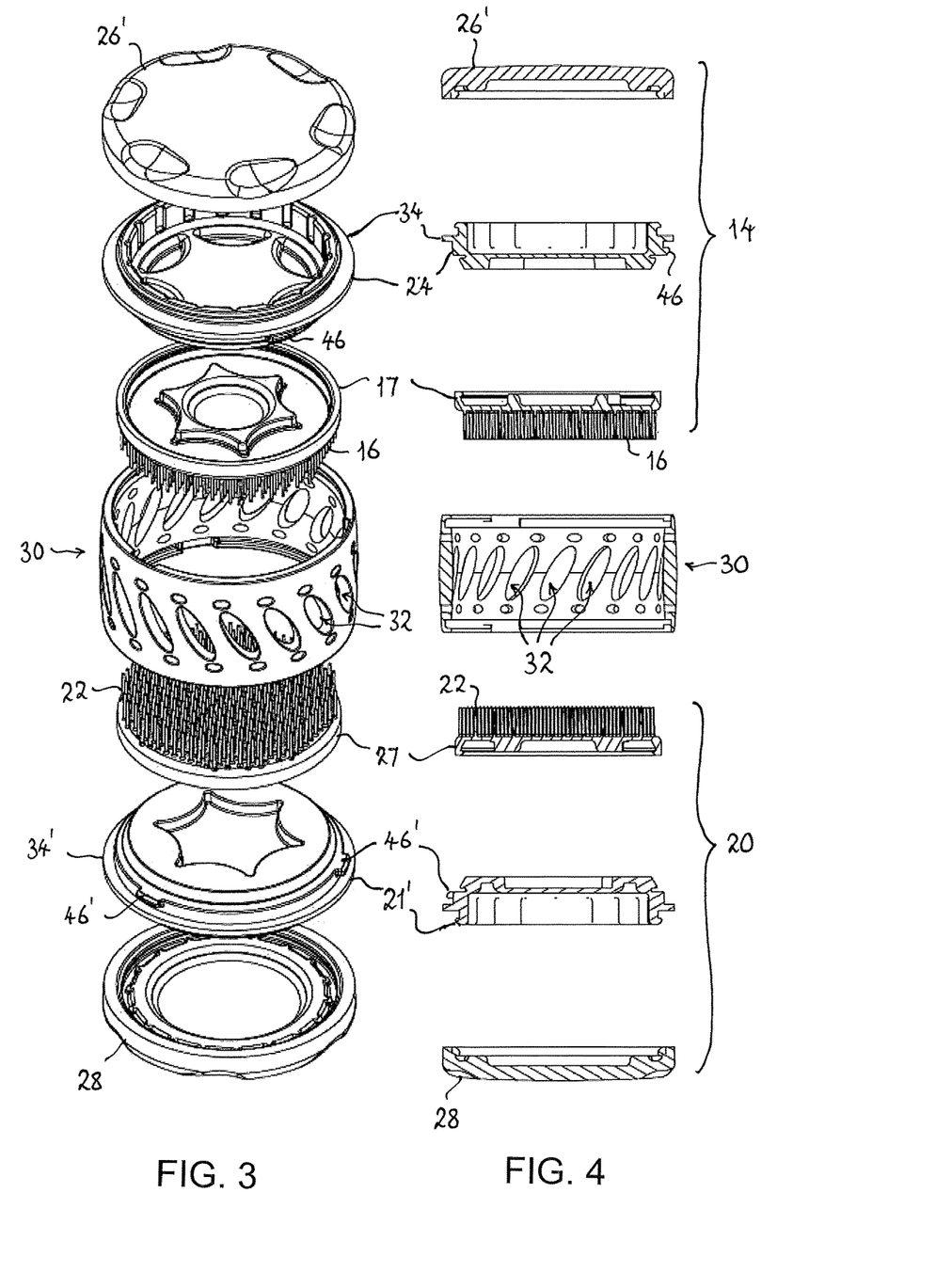
FIG. 3 is an exploded view of the cleaning device of FIG. 1.
FIG. 4 is a section view through each of the components of the cleaning device of FIG. 2 shown in an exploded view.

Preferably the lower cleaning brush 20 further comprises a lower base component 21' having the upwardly protruding bristles 22 provided in connection with an upper side of the base component, and a lower handle 28 provided in connection with a lower side of the base component 21. The handle 28 clips onto the lower side of the base component 21, as can be seen most clearly in FIGS. 2(d) and 3. As with the upper handle 26', the lower handle 28 can be replaced with a different type of handle if required. As with the upper cleaning brush 14, the upwardly protruding bristles 22 are moulded separately, from a suitably resilient rubber, silicon or plastics material with the required stiffness to effect the cleaning action. The bristles 22 protrude from a web 27 of the same material, which clips onto the upper side of the base component 21, as can be seen most clearly in FIGS. 2(*d*), 3 and 4.

Unlike the first embodiment, in this embodiment of the cleaning device 50, the upper cleaning brush 14 and the lower cleaning brush 20 are of substantially identical design and construction. This simplifies and reduces the cost of manufacturing the components. It also means that the various components of the upper and lower cleaning brushes are interchangeable, which makes it easier for the user to disassemble and reassemble the cleaning device 10.

The downwardly protruding bristles 16 on the upper cleaning brush 14 and/or the upwardly protruding bristles 22 on the lower cleaning brush 20 may include a plurality a bristles of varying height, diameter and/or stiffness, which are adapted to accommodate and clean different types of removable dental appliance during the cleaning action. In any case, the bristles 16, 22 limit the degree of rotation of the dental appliance that occurs while the rotatable cleaning brushes 14 and 20 clean the upper and lower surfaces of the appliance. As the rotatable upper and lower cleaning brushes are both "worked" in a clockwise and then an anticlockwise manner, the appliance moves backwards and forwards across the upper and lower cleaning brushes 14 and 20. The appliance may thus move back and forth within limits during the cleaning action. This facilitates the simultaneous cleaning action on "all surfaces" of the dental appliance. In practice, it was found that the anti-rotation pillars 29 of the first embodiment are not necessary.

Figure 7:
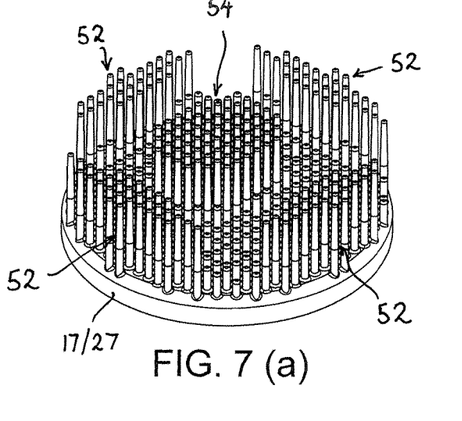
FIG. 7(a) is a top perspective view of an alternative brush design for the cleaning device of FIG. 2.
FIG. 7(b) is a side elevation view of the brush shown in FIG. 7(a)
FIG. 7(c) is a top plan view of the brush shown in FIG. 7(a)
FIG. 7(d) is a section view of the brush through the line G-G in FIG. 7(c)

FIGS. 7(*a*) to 7(*d*) illustrate an alternative cluster brush configuration for the upwardly protruding bristles 22 on the lower cleaning brush 20 and/or the downwardly protruding bristles 16 on the upper cleaning brush 14. This brush configuration is particularly suited for cleaning full and partial dentures. In this embodiment the bristles are arranged in clusters, including a plurality of peripheral clusters 52 and a single central cluster 54 of bristles of relatively increased height, surrounded by troughs 56 formed by bristles of relatively reduced height in between so as to form one or more recesses within which the removable dental appliance can be more readily accommodated. In use, a denture is placed with the teeth received in the troughs 56 formed between the central cluster 54 and the peripheral clusters 52, and with the base of the denture supported on the central cluster 54.

The cleaning device 50 further comprises a casing connector 30 for temporarily rotatably interconnecting the rotatable upper cleaning brush 14 and the lower cleaning brush 20 so as to form a single integrated unit when assembled. Preferably the rotatable interconnection of the rotatable upper cleaning brush 14 with the casing connector 30 is facilitated by a raised guide rail 34 provided on the base component 24 of the rotatable upper cleaning brush 14, as can be seen most clearly in FIGS. 2(*b*), 2(*d*) and 4. In its assembled position, an upper edge of the cylindrical housing 30 abuts against the raised guide rail 34, as shown in FIGS. 2(*b*) and 2(*d*). Preferably the rotatable interconnection of the rotatable lower cleaning brush 20 with the casing connector 30 is likewise facilitated by a raised guide rail 34' provided on the base component 21' of the rotatable lower cleaning brush 20, as can be seen most clearly in FIGS. 2(*b*), 2(*d*) and 4. In its assembled position, a lower edge of the cylindrical housing 30 abuts against the raised guide rail 34', as shown in FIGS. 2(*b*) and 2(*d*). The cylindrical housing 30 is provided with first and second internal grooves 38, 40, as can be seen most clearly in FIGS. 4(*b*) and 4(*d*).

The rotatable interconnection and assembly of the lower cleaning brush 20 with the casing connector 30 is substantially identical to that of the upper cleaning brush 14. Therefore the like parts for the rotatable interconnection of the lower cleaning brush 20 are identified with the same reference numerals, and will not be described again in detail.

Typically the cleaning device 50 further comprises a locking mechanism 44 for locking the casing connector 30 to the rotatable upper cleaning brush 14 and to the rotatable lower cleaning brush 20 to permit rotation of the upper and lower cleaning brushes relative to the casing connector without the device coming apart. Typically the locking mechanism 44 comprises a 'push, turn and click' locking mechanism provided adjacent to the raised guide rails 34 and 34' on the rotatable upper and lower cleaning brushes. The 'push, turn and click' locking mechanism 44 is similar to that of the previous embodiment, and comprises a plurality lock protrusions 46 provided on the lower and upper base components 21, 24, and a matching plurality of interlocking recesses 42 provided in the internal grooves 38 and 40 of the casing connector 30. The lock protrusions 46, 46' are provided adjacent to the raised guide rails 34, 34', as shown in FIGS. 3 and 4, and are adapted to be slidably received in either one of the first and second internal grooves 38 and 40 respectively.

In order to rotatably connect the rotatable upper cleaning brush 14 or the rotatable lower cleaning brush 20 to the casing connector 30 the lock protrusions 46 are first aligned with the interlocking recesses 42. Then the cleaning brush 14 or 20 and casing connector 30 are pushed together and rotated relative to each other, so that the lock protrusions 46 ride over stops 48 provided at the sides of the interlocking recesses 42, and thereby the cleaning brush and the casing connector 30 'lock' together. Once the lock protrusions 46 are received in the internal groove 38 or 40, they are free to slidably move in the grooves between the stops 48.

A straight rotation action of the cleaning brush 14 or 20 will not release it from the guide rail 34. The rotation of the cleaning brush reaches its limit when the lock protrusions 46 strike the stops 48. The rotatable cleaning brush would then be rotated back the other way until the lock protrusions 46 again reach the stops 48. This back and forth rotation of the cleaning brushes 14 and 20 relative to the casing connector 30 is a preferred cleaning cycle.

To release the 'push, turn and click' locking mechanism 44, the base component of the cleaning brush must be slightly depressed (squeezed) so that the lock protrusions 46 "duck" under the stops 48 and can thus be realigned with the interlocking recesses 42 to release the cleaning brush from the casing connector 30.

Advantageously, in its assembled condition, the cleaning device 10 effectively 'locks' a dental appliance in place inside of the 'caddy-like' cylindrical housing 30, in the cleaning region between the rotatable upper cleaning brush 14 and the lower cleaning brush 20.

A method of using the dental cleaning device 50 will now be described. The dental appliance (not shown) is placed into the rotatable lower cleaning brush 20 of the device 50, with the lower cleaning brush 20 and the cylindrical housing 30 already rotatably interlocked. The rotatable upper cleaning brush 14 is then locked into place, so that the appliance is securely and safely held in the device 10 ready for cleaning. The correct cleaning solution is then applied through the perforations 32 of the cylindrical housing. The closed and locked unit 50 is then held under running water, (so that fresh water is always being used to clean and rinse the appliance) and the upper and lower cleaning brushes are twisted in a clockwise/counter-clockwise fashion for 15 to 30 seconds. The alternating twisting action and dual opposing bristles ensure all surfaces of the appliance are effectively cleaned simultaneously. Once cleaned and rinsed the appliance remains safely stored in the device, and will air dry until further use is required. The entire cleaning device 10 can be soaked in a solution if desired by placing it in a suitable soaking bath.

Figure 8:
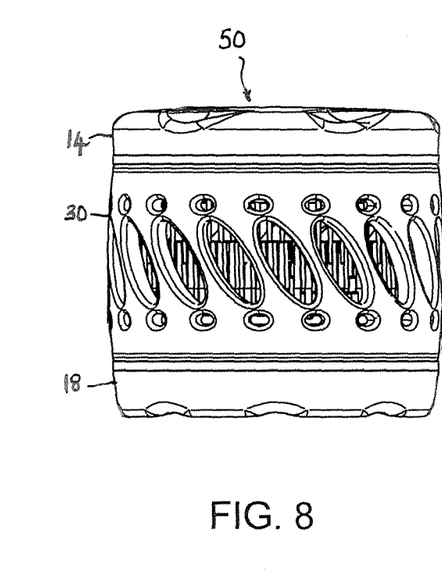
FIG. 8 is a side elevation view of the second embodiment of the dental cleaning device shown in FIG. 2.
Figure 9:
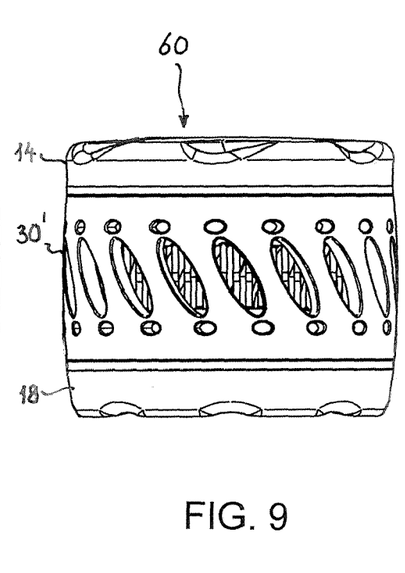
FIG. 9 is a side elevation view of a third embodiment of a dental cleaning device in accordance with the present invention; and, FIG. 10 is a side elevation view of a fourth embodiment of a dental cleaning device in accordance with the present invention.

A third embodiment of a cleaning device 60, for cleaning a removable dental appliance (not shown), in accordance with the invention, is illustrated in FIG. 9. The cleaning device 60 is substantially identical to the second embodiment 50, except that the cleaning device 60 is of similar diameter but lower profile dimensions to accommodate smaller removable dental appliances, such as occlusal splints and other single arch appliances. The overall height of the cleaning device 60 is 71.85 mm, and the overall diameter of the device is 86.53 mm. The second embodiment of the device 50 is shown in FIG. 8 to the same scale for ease of comparison. The overall height of the cleaning device 50 is 79.82 mm, and the overall diameter of the device is 87.04 mm. The third embodiment of the cleaning device 60 comprises substantially the same components and construction as the second embodiment, and therefore the same reference numerals will be used to identify the similar parts.

The cleaning device 60 comprises a rotatable upper cleaning brush 14 comprising a plurality of downwardly protruding bristles 16 for cleaning an upper surface of the removable dental appliance.

A lower dental appliance holder 18 is provided for holding the dental appliance and to inhibit movement of the dental appliance relative to the rotatable upper cleaning brush 14 wherein, in use, a cleaning action can be applied to the dental appliance by rotating the rotatable upper cleaning brush 14 relative to the dental appliance. As with the second embodiment, the lower dental appliance holder 18 comprises a lower cleaning brush 20 substantially identical to the upper cleaning brush 14, having a plurality of upwardly protruding bristles 22 for cleaning a lower surface of the dental appliance. In use, rotation of the rotatable upper cleaning brush 14 and the lower cleaning brush 20 relative to the dental appliance ensures that a simultaneous cleaning action is applied to both the upper and the lower surfaces of the dental appliance.

As with the previous embodiments, a casing connector in the form of a cylindrical housing 30' is provided in the cleaning device 60 for temporarily rotatably interconnecting the rotatable upper cleaning brush 14 and the lower cleaning brush 20 so as to form a single integrated unit when assembled, as shown in FIG. 9. As can be seen by comparing the device 60 shown in FIG. 9 with the device 50 shown in FIG. 8, the casing connector 30' is of similar diameter to the casing connector 30, but of reduced height to effectively accommodate, and perform a cleaning action on, smaller dental appliances. It is primarily the feature of the casing connector that enables the dimensions of the cleaning device to be modified for various types of removable dental appliance, without any changes in the basic design, assembly and function of the various components of the device.

In other respects the design, assembly and operation of the cleaning device 60 is substantially identical to that of the second embodiment 50, and will not be described again in detail.

Figure 10:
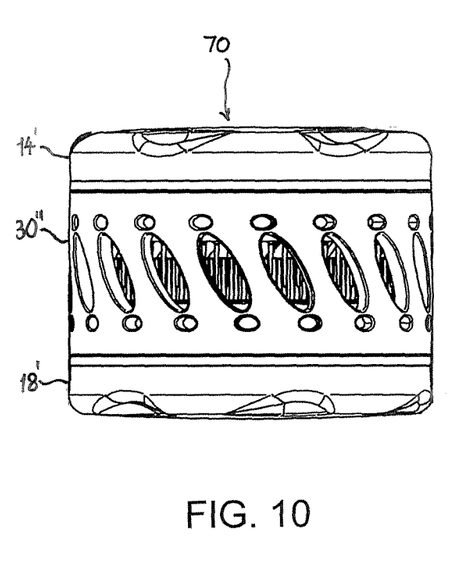

A fourth embodiment of a cleaning device 70 for cleaning a removable dental appliance (not shown), in accordance with the invention, is illustrated in FIG. 10. The cleaning device 70 is substantially identical to the second embodiment 60, except that the cleaning device 70 is of larger diameter and has lower profile dimensions to accommodate lower profile removable dental appliances, such as orthodontic retainers, Invisalign™ type appliances, or tooth whitening stents. The cleaning device 70 is of similar height (profile) as the third embodiment 60. The overall height of the cleaning device 70 is 73.95 mm, and the overall diameter of the device is 93.89 mm. This embodiment of the cleaning device 70 also comprises substantially the same components as the second and third embodiments 50 and 60, and therefore the same reference numerals will again be used to identify the similar parts and will not be described again in detail.

The cleaning device 70 comprises a rotatable upper cleaning brush 14' comprising a plurality of downwardly protruding bristles 16 for cleaning an upper surface of the removable dental appliance. A lower dental appliance holder 18' in the form of lower cleaning brush 20' is provided for holding the dental appliance and which is used in connection with the rotatable upper cleaning brush to inhibit movement of the dental appliance relative to the rotatable upper cleaning brush 14' wherein, in use, a cleaning action can be applied to the dental appliance by rotating the rotatable upper cleaning brush 14 relative to the dental appliance. As with the previous embodiments, the lower cleaning brush 20' has a plurality of upwardly protruding bristles 22 for cleaning a lower surface of the dental appliance. In use, rotation of the rotatable upper cleaning brush 14' and the lower cleaning brush 20' relative to the dental appliance ensures that a simultaneous cleaning action is applied to both the upper and the lower surfaces of the dental appliance. This embodiment of the cleaning device 70 is most suitable for cleaning two low profile oral appliances at the same time, in essentially the same way as that described for the cleaning of a single device.

As with the previous embodiments, a casing connector or cylindrical housing 30" is provided in the cleaning device 70 for temporarily rotatably interconnecting the rotatable upper cleaning brush 14' and the lower cleaning brush 20' so as to form a single integrated unit when assembled, as shown in FIG. 10.

In other respects the design, assembly and operation of the cleaning device 70 is substantially identical to that of the second and third embodiments 50 and 60, and will not be described again in detail.

The cluster brush configuration of FIGS. 7(a) to 7(d), employed in the second embodiment of the cleaning device 50, is particularly suited to dentures. The third and fourth embodiments of the cleaning device 60 and 70 preferably have regular, uniform brush configurations. Various brush configurations can be used for other types of removable dental appliances. For example, another embodiment of the cleaning device, designed for cleaning a sports mouthguard, combines a cluster brush configuration on one of the upper or lower rotatable cleaning brushes, with an opposing regular brush configuration on the other rotatable cleaning brush.

Now that several preferred embodiments of the dental cleaning device have been described in detail, it will be apparent that the described embodiments provide a number of advantages over the prior art, including the following:

a) Provide safe, effective and efficient cleaning, storing and protection for all manner of removable dental appliances;

b) More effective cleaning by utilising custom-designed brushing action that cleans fitting and functional appliance surfaces simultaneously with custom formulated cleaning and sanitising solutions;

c) Safer than the handheld brush method in that the cleaning device locks the appliance in place inside of a caddy-like cylindrical housing. The 'caddy' is full-hand size, ergonomically designed and protects the appliance from any damage incurred from dropping and/or inadvertent distortion, cracking or breakage from hand pressure whist gripping the appliance during traditional methods of appliance cleaning;

d) Faster than any other typical cleaning option. In 15-30 seconds the cleaning device will accomplish what takes 5 to 8 minutes to do properly using the conventional handheld brushing method, or overnight using a soaking bath. (Dental professionals do not recognize 'overnight soaking' as a stand-alone cleaning method, but acknowledge widespread use.); and e) The alternating twisting action and dual opposing brushes ensure all surfaces of the dental appliance are effectively cleaned and rinsed simultaneously. Once cleaned and rinsed the appliance can remain safely stored in the device until further use is required. The entire cleaning device can be soaked in a solution if desired.

It will be readily apparent to persons skilled in the relevant arts that various modifications and improvements may be made to the foregoing embodiments, in addition to those already described, without departing from the basic inventive concepts of the present invention. For example, whilst the described cleaning device is operated by a manual twisting action, the relative rotation of the upper and/or lower cleaning brushes could be motorised to provide an automatic cleaning action. Therefore, it will be appreciated that the scope of the invention is not limited to the specific embodiments described.

The invention claimed is:

1. A cleaning device for cleaning a removable dental appliance, the device comprising:
   a rotatable upper cleaning brush comprising a plurality of downwardly protruding bristles for cleaning an upper surface of a removable dental appliance;
   a lower dental appliance holder for holding the dental appliance and which is used in connection with the rotatable upper cleaning brush to limit movement of the dental appliance relative to the rotatable upper cleaning brush;
   a casing connector for temporarily rotatably interconnecting the rotatable upper cleaning brush and the lower dental appliance holder so as to form a single integrated unit wherein, in use, a cleaning action can be applied to the dental appliance by rotating the rotatable upper cleaning brush and/or the lower dental appliance holder relative to the dental appliance; and
   wherein the casing connector comprises a generally cylindrical housing for enclosing a cleaning region between the rotatable upper cleaning brush and the lower dental appliance holder, and the generally cylindrical housing having a plurality of perforations so as to permit fluid to flow through the casing connector to the dental appliance held in the cleaning region.

2. A cleaning device as defined in claim 1, wherein the cylindrical housing is manufactured of a substantially transparent material wherein, in use, the cleaning region between the rotatable upper cleaning brush and the lower dental appliance holder is generally visible to the user during use.

3. A cleaning device as defined in claim 1, wherein the casing connector is adapted to be rotatably interconnected to both the rotatable upper cleaning brush and the lower dental appliance holder.

4. A cleaning device as defined in claim 1, wherein the rotatable interconnection is facilitated by a raised guide rail on the upper cleaning brush and first and second internal grooves in the casing connector.

5. A cleaning device as defined in claim 4, wherein the cleaning device further comprises a locking mechanism for locking the casing connector to the rotatable upper cleaning brush to permit rotation of the upper cleaning brush relative to the casing connector without the device coming apart.

6. A cleaning device as defined in claim 5, wherein the locking mechanism comprises a 'push, turn and click' locking mechanism provided adjacent to the raised guide rail on the rotatable upper cleaning brush.

7. A cleaning device as defined in claim 6, wherein the 'push, turn and click' locking mechanism comprises a plurality of lock protrusions provided on the upper cleaning brush, and a matching plurality of interlocking recesses provided in at least one of the first and second internal grooves of the casing connector.

8. A cleaning device as defined in claim 4, wherein an annular lip is provided on the lower dental appliance holder, the annular lip being received in one of the first and second internal grooves of the casing connector by a simple friction fit since the lower dental appliance holder is not required to rotate relative to the casing connector.

9. A cleaning device as defined in claim 4, wherein the rotatable interconnection is also facilitated by a raised guide rail on the lower dental appliance holder and a locking mechanism for locking the casing connector to the lower dental appliance holder to permit rotation of the lower dental appliance holder relative to the casing connector without the device coming apart.

10. A cleaning device as defined in claim 1, wherein both the rotatable upper cleaning brush and the lower dental appliance holder can be handheld, and the relative rotation of the rotatable upper cleaning brush and/or the lower dental appliance holder can be effected by a simple back and forth twisting action of the hands.

11. A cleaning device as defined in claim 1, wherein the lower dental appliance holder comprises a lower cleaning brush having a plurality of upwardly protruding bristles for cleaning a lower surface of the dental appliance whereby, in use, rotation of the rotatable upper cleaning brush and of the lower cleaning brush relative to the dental appliance ensures that a simultaneous cleaning action is applied to both the upper and the lower surfaces of the dental appliance.

12. A cleaning device as defined in claim 11, wherein the lower cleaning brush further comprises a lower base component having the upwardly protruding bristles provided in connection with an upper side of the base component, and a handle provided in connection with a lower side of the base component.

13. A cleaning device as defined in claim 12, wherein both the rotatable upper cleaning brush and the rotatable lower cleaning brush are of substantially identical design and construction.

14. A cleaning device as defined in claim 12, wherein the downwardly and upwardly protruding bristles provided on the upper and lower cleaning brushes respectively are adapted to interleave as the upper and lower cleaning brushes are rotated relative to each other to ensure that deep, harder-to-reach areas of the dental appliance are reached and thoroughly cleaned.

15. A cleaning device as defined in claim 14, wherein the bristles on either one or both of the upper and lower cleaning brushes are tapered so that during relative rotation they intermittently interleave.

16. A cleaning device as defined in claim 12, wherein the bristles on either one or both of the upper and lower cleaning brushes are arranged in clusters, including a plurality of peripheral clusters, and a single central cluster of bristles of relatively increased height surrounded by troughs formed by bristles of relatively reduced height in between so as to form one or more recesses within which the removable dental appliance can be more readily accommodated.

17. A cleaning device as defined in claim 1, wherein both the rotatable upper cleaning brush and the lower dental appliance holder are of substantially circular configuration.

18. A cleaning device as defined in claim 1, wherein the rotatable upper cleaning brush further comprises an upper base component having the downwardly protruding bristles provided in connection with a lower side of the base component, and a handle provided in connection with an upper side of the base component.

19. A cleaning device as defined in claim 18, wherein the handle is ergonomically designed for a left-handed or right-handed user as required.

20. A cleaning device as defined in claim 19, wherein the handle is manufactured from a suitable soft, non-slip material to provide a comfortable and secure grip in use when either wet or dry.

* * * * *